US012575743B2

(12) United States Patent
Sabbagh

(10) Patent No.: US 12,575,743 B2
(45) Date of Patent: Mar. 17, 2026

(54) SYSTEMS AND METHODS FOR ASSESSING HEART AND RESPIRATORY DISORDERS

(71) Applicant: Roland Sabbagh, Ottawa (CA)

(72) Inventor: Roland Sabbagh, Ottawa (CA)

(*) Notice: Subject to any disclaimer, the term of this patent is extended or adjusted under 35 U.S.C. 154(b) by 657 days.

(21) Appl. No.: 17/598,631

(22) PCT Filed: Mar. 25, 2020

(86) PCT No.: PCT/CA2020/050389

§ 371 (c)(1),
(2) Date: Sep. 27, 2021

(87) PCT Pub. No.: WO2020/191490

PCT Pub. Date: Oct. 1, 2020

(65) Prior Publication Data

US 2022/0183575 A1 Jun. 16, 2022

(30) Foreign Application Priority Data

Mar. 26, 2019 (CA) ................................ CA 3038097

(51) Int. Cl.
| | |
|---|---|
| *A61B 5/00* | (2006.01) |
| *A61B 5/0205* | (2006.01) |
| *A61B 5/024* | (2006.01) |
| *A61B 5/08* | (2006.01) |
| *G16H 30/40* | (2018.01) |

(Continued)

(52) U.S. Cl.
CPC ........ *A61B 5/02055* (2013.01); *A61B 5/0013* (2013.01); *A61B 5/0077* (2013.01);

(Continued)

(58) Field of Classification Search
None
See application file for complete search history.

(56) References Cited

U.S. PATENT DOCUMENTS

| | | | |
|---|---|---|---|
| 2005/0197552 A1 | 9/2005 | Baker, Jr. | |
| 2014/0221845 A1* | 8/2014 | Mestha | .............. A61B 5/02416 |
| | | | 600/479 |

(Continued)

FOREIGN PATENT DOCUMENTS

| | | |
|---|---|---|
| EP | 3375351 A1 | 9/2018 |
| WO | 2013027027 A2 | 2/2013 |
| WO | 2018166788 A1 | 9/2018 |

OTHER PUBLICATIONS

International Search Report for related PCT Application No. PCT/CA2020/050389, date mailed Jun. 30, 2020, 3 pages.

(Continued)

*Primary Examiner* — Sana Sahand
(74) *Attorney, Agent, or Firm* — Tucker Ellis LLP

(57) ABSTRACT

The present disclosure describes systems and methods for assessing heart and respiratory disorders in a patient using a video analysis tool to analyze video data taken of the patients neck region. The video analysis tool allows for an accurate, objective assessment of the patient. In some aspects of the present disclosure, a clinician may capture video data of the patients neck region and run the video analysis tool. Additionally or alternatively, the system may be implemented remotely whereby the video analysis tool may be executed remotely from the video recording device. The video analysis tool extracts pulsatile signals in the neck region from the video data and determines pulsatile signals of interest for assessing heart and respiratory disorders in the patient. The video analysis tool generates assessment data based on the pulsatile signals of interest.

23 Claims, 13 Drawing Sheets

400

Divide neck region into plural sub-regions — 402

Extract pulsatile signals for each sub-region — 404

Extract features of pulsatile signals — 406

Classify pulsatile signals — 408

Determine assessment result — 410

(51) Int. Cl.
    G16H 50/20      (2018.01)
    G16H 50/30      (2018.01)

(52) U.S. Cl.
    CPC ........ A61B 5/02416 (2013.01); A61B 5/0816 (2013.01); A61B 5/7264 (2013.01); G16H 30/40 (2018.01); G16H 50/20 (2018.01); G16H 50/30 (2018.01); *A61B 2576/02* (2013.01)

(56) References Cited

U.S. PATENT DOCUMENTS

| | | | |
|---|---|---|---|
| 2014/0275832 A1* | 9/2014 | Muehlsteff ........... | A61B 5/6889 600/301 |
| 2016/0171684 A1* | 6/2016 | De Haan ............... | G06T 7/0012 382/103 |
| 2016/0253820 A1* | 9/2016 | Jeanne .................. | G06T 7/0012 382/107 |
| 2018/0177464 A1* | 6/2018 | DeBusschere ......... | A61B 5/021 |

OTHER PUBLICATIONS

Ruminski, J. et al., "Evaluation of Facial Pulse Signals using Deep Neural Net Models," 2019 41st Annual International Conference of the IEEE Engineering in Medicine and Biology Society (EMBC), Jul. 27, 2019, pp. 3399-3403, [retrieved on May 11, 2020], Retrieved from: <doi:10.1109/EMBC.2019.8857839>.
European Search Report for related PCT Application No. PCT/CA2020/050389, date mailed Nov. 14, 2022, 9 pages.

\* cited by examiner

<u>300</u>

400

Divide neck region into plural sub-regions — 402

Extract pulsatile signals for each sub-region — 404

Extract features of pulsatile signals — 406

Classify pulsatile signals — 408

Determine assessment result — 410

440

Identify pulsatile signals corresponding to JVP — 442

Perform frequency analysis — 444

Strong frequency at frequency 2x heart rate? — 446

YES — 448 — Confirm JVP with CHF

NO — 450 — Potential CHF with atrial fibrilation

460

500

Display indications for recording video data — 502

Record video data of patient — 504

Upload recorded data — 506

Display assessment data — 508

600a

600c

SYSTEMS AND METHODS FOR ASSESSING HEART AND RESPIRATORY DISORDERS

This application is a national phase application of International Application No PCT/CA2020/050389, filed Mar. 25, 2020, which claims priority to Canadian Patent Application Serial No. 3038097, filed Mar. 26, 2019, all of which are incorporated herein by reference.

TECHNICAL FIELD

The present disclosure relates to assessing heart and respiratory disorders in a patient, and in particular to providing an objective assessment of heart and respiratory disorders.

BACKGROUND

Examination of jugular veins in a patient's neck is one of the most specific indicators of heart failure decompensation. The most common cause of heart failure of the right side of the heart is in fact back pressure of blood from a failing left ventricle. If the left ventricle fails, fluid buildup in the lungs may result in a back pressure that is too much for the right side of the heart to push blood into the lungs due to too much congestion. When the right ventricle fails to push blood into the lungs, the blood pushes back into the superior and inferior vena cava, causing congestion of the liver and then the pressure goes up a column of blood called the superior vena cava and subsequently into the jugular veins in the neck. Accordingly, the jugular veins can provide an indirect measure of the failing right heart or at a minimum, a defective tricuspid valve, constrictive pericarditis, restrictive cardiomyopathy or volume overload from kidney or liver failure.

However, examination of the jugular veins to identify heart failure is subjective and fraught with poor inter-observer reproducibility. Different clinicians may observe the pulsations differently and/or interpret the results of the observation differently. Accordingly, systems and methods that enable objective assessment of heart and respiratory disorders remain highly desirable.

SUMMARY

In accordance with one aspect of the present disclosure, a computer-implemented method for assessing heart and respiratory disorders in a patient is disclosed, comprising: receiving video data of a neck region of the patient; extracting a pulsatile signal for each of a plurality of sub-regions of the neck region from the video data; extract features from each pulsatile signal; determining one or more pulsatile signals of interest for assessing heart and respiratory disorders in the patient by classifying the pulsatile signals based on the extracted features; generating assessment data based on the one or more pulsatile signals of interest; and outputting the assessment data.

In some aspects of the method, the assessment data comprises at least one of: the one or more pulsatile signals of interest, and a heat map of the neck region of the patient highlighting the one or more pulsatile signals of interest.

In some aspects the method further comprises determining an assessment result of heart and respiratory disorder in the patient based on the one or more pulsatile signals of interest.

In some aspects of the method, the assessment data comprises the assessment result.

In some aspects the method further comprises extracting at least one of a heart rate and a respiration rate of the patient from the video data; and wherein determining the assessment result is further based on the at least one of the heart rate and the respiration rate.

In some aspects of the method, the assessment data comprises one or both of the heart rate and the respiration rate.

In some aspects the method further comprises: receiving supplemental patient data for the patient; and wherein determining the assessment result is further based on the supplemental patient data.

In some aspects of the method, the assessment result is an arrhythmia, determined based on a time difference between consecutive pulse peaks of the one or more pulsatile signals of interest.

In some aspects of the method, determining the assessment result is further based on historical assessment data generated from previously received video data.

In some aspects the method further comprises determining a recommended action based on the assessment result; and wherein the assessment data comprises the recommended action.

In some aspects of the method, the one or more pulsatile signals of interest correspond to an artery or a vein in the patient's neck region.

In some aspects of the method, the features extracted from the pulsatile signal include one or more of: an amplitude, a frequency, a shape of a pulse, a power level, and a second harmonic of the pulsatile signal.

In some aspects of the method, the video data is received from a remote computing device, and wherein outputting the assessment data comprises transmitting the assessment data to the remote computing device for display.

In accordance with another aspect of the present disclosure, a non-transitory computer-readable medium is disclosed having computer-readable instructions stored thereon, which when executed by a processing device, configure the processing device to perform the above method.

In accordance with another aspect of the present disclosure, a system for assessing heart and respiratory disorders in a patient is disclosed, comprising: a processing unit; and a memory having computer-readable instructions stored thereon, which when executed by the processing unit configure the system to: receive video data of a neck region of the patient; extract a pulsatile signal for each of a plurality of sub-regions of the neck region from the video data; extract features from each pulsatile signal; determine one or more pulsatile signals of interest for assessing heart and respiratory disorders in the patient by classifying the pulsatile signals based on the extracted features; generate assessment data based on the one or more pulsatile signals of interest; and output the assessment data.

In some aspects of the system, the assessment data comprises at least one of: the one or more pulsatile signals of interest, and a heat map of the neck region of the patient highlighting the one or more pulsatile signals of interest.

In some aspects of the system, the system is further configured to determine an assessment result of heart and respiratory disorder in the patient based on the one or more pulsatile signals of interest.

In some aspects of the system, the assessment data comprises the assessment result.

In some aspects of the system, the system is further configured to: extract at least one of a heart rate and a respiration rate of the patient from the video data; and wherein determining the assessment result is further based on the at least one of the heart rate and the respiration rate.

In some aspects of the system, the assessment data comprises one or both of the heart rate and the respiration rate.

In some aspects of the system, the system is further configured to: receive supplemental patient data for the patient; and wherein determining the assessment result is further based on the supplemental patient data.

In some aspects of the system, the assessment result is an arrhythmia, determined based on a time difference between consecutive pulse peaks of the one or more pulsatile signals of interest.

In some aspects of the system, the system is further configured to determine the assessment result based on historical assessment data generated from previously received video data.

In some aspects of the system, the system is further configured to: determine a recommended action based on the assessment result; and wherein the assessment data comprises the recommended action.

In some aspects of the system, the one or more pulsatile signals of interest correspond to an artery or a vein in the patient's neck region.

In some aspects of the system, the features extracted from the pulsatile signal include one or more of: an amplitude, a frequency, a shape of a pulse, a power level, and a second harmonic of the pulsatile signal.

In some aspects of the system, the video data is received from a remote computing device, and wherein outputting the assessment data comprises transmitting the assessment data to the remote computing device for display.

BRIEF DESCRIPTION OF THE DRAWINGS

Further features and advantages of the present disclosure will become apparent from the following detailed description, taken in combination with the appended drawings, in which.

It will be noted that throughout the appended drawings, like features are identified by like reference numerals.

DETAILED DESCRIPTION

Figure 1:
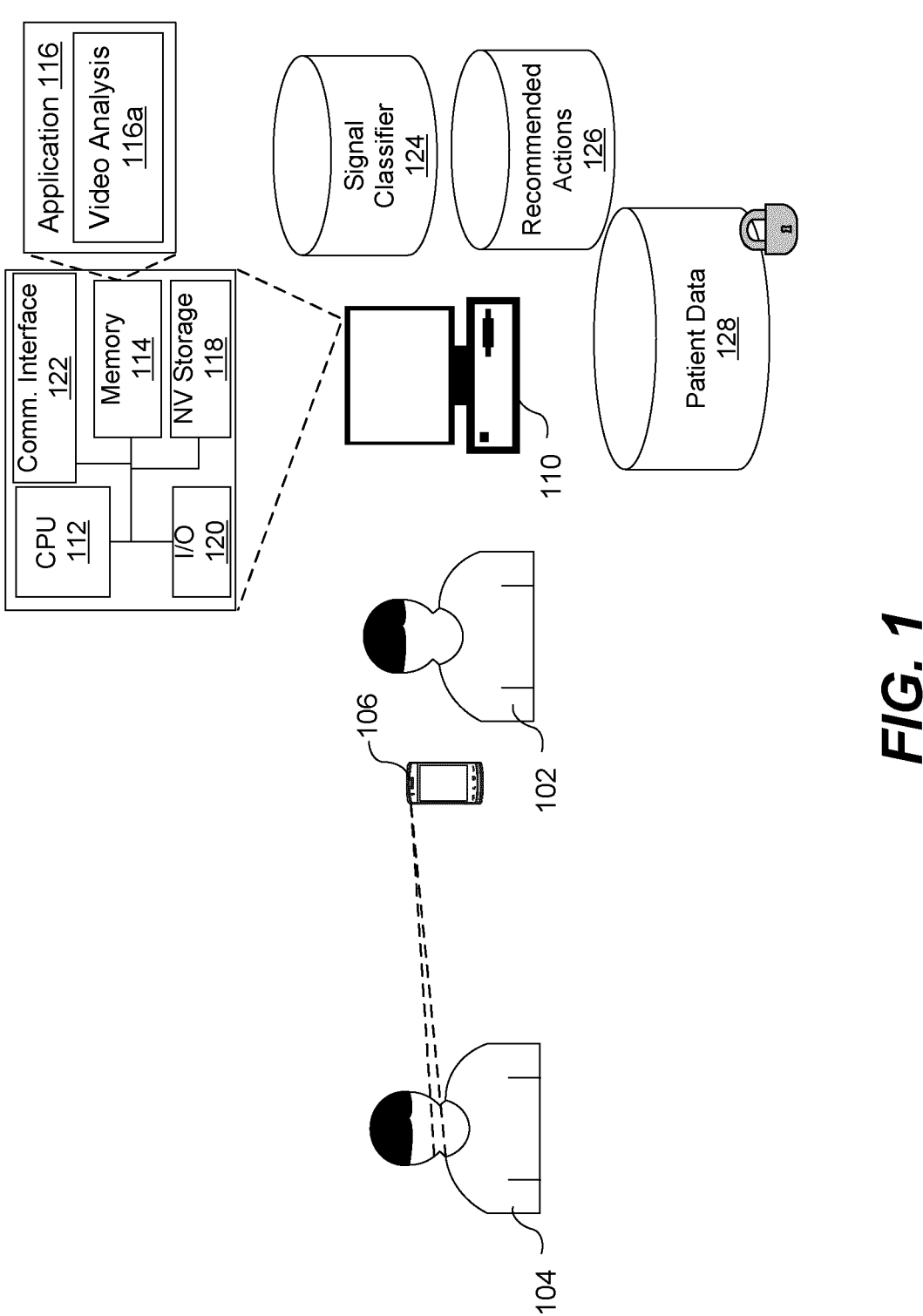
FIG. 1 shows a representation of a system for assessment of heart and respiratory disorders in accordance with some aspects of the present disclosure.

The present disclosure describes systems and methods for assessing heart and respiratory disorders in a patient using an artificial intelligence (AI) video analysis tool to analyze video data taken of the patient's neck region. The video analysis tool allows for an accurate, objective assessment of the patient. The video analysis tool may be initially trained using a clinician's diagnosis and/or measured physical parameters of the patient (e.g. heart rate, ultrasound imaging, etc.) to generate criteria used for classification of signals, and with enough data the video analysis tool can apply neural network or deep learning as a classifier for performing classification by itself. The video analysis tool can generate assessment data that enables objective assessments of heart and respiratory disorders in the patient and may also provide recommended actions. The video analysis tool is capable of providing accurate outputs without requiring expensive equipment to capture the video data and without requiring any secondary equipment such as medical equipment that concurrently measure physical parameters of the patient. As such, the video data may be captured using various video recording devices, including but not limited to a mobile phone, a tablet, a computer, a digital camera, webcam, etc., allowing for flexibility in the implementation of the system that can be readily adopted by end-users.

In some aspects of the present disclosure, a clinician may capture video data of the patient's neck region and run the video analysis tool. The video analysis tool extracts pulsatile signals in the neck region from the video data and determines pulsatile signals of interest for assessing heart and respiratory disorders in the patient, and generates assessment data for output based on the pulsatile signals of interest. Additionally or alternatively, the system may be implemented remotely whereby the video analysis tool may be executed remotely from the video recording device. Video data captured by a clinician may be securely transmitted from a clinician's computing device to a remote analysis system running the video analysis tool for real-time analysis. Further, a patient may themselves capture the video data and securely transmit the video data from a patient's computing device to the remote analysis system for analysis. When the patient captures the video data using the patient's computing device, the patient may receive an assessment of heart and/or respiratory disorders and be provided with recommended actions in real-time without having to physically visit a doctor's office.

Capture and transmission of the video data, as well as output of the assessment data, may be facilitated through an application running on the clinician's computing device and/or the patient's computing device. The patient data including the video data and/or assessment data may be securely stored locally or at the remote analysis system. When the video data is captured by the patient, the patient's doctor may access the remote analysis system using the application to review the patient's data. The remote analysis system may also push notifications to the patient's doctor, such as whenever a video analysis has been performed, when there any changes to the patient's assessment, and/or when there is a recommended action. Such data may also be pushed to the doctor's office for local storage in association with the patient's records.

Accordingly, the present disclosure allows for an objective assessment of heart and respiratory disorders in the patient, which may be provided remotely without requiring visual observation of the patient by a clinician, and which may be provided in real-time or near real-time. The video analysis tool provides assessment data for assessing such heart and respiratory disorders, and may further provide recommended actions to the patient. Continued assessment and monitoring, without visits to the clinician, can thus be provided. An application running on the patient's computing device can also be used as a source of education to educate the patient on heart and respiratory disorders.

While the present disclosure may in particular make reference to assessing certain types of heart and respiratory disorders in a patient, such as congestive heart failure (CHF) by examining jugular venous pulsations (JVP) in the patient's neck region, a person skilled in the art will recognize that various other heart and respiratory disorders can be determined from an analysis of the video data. For example, elevated levels of jugular venous pulsations may be indicative of other clinical conditions such as kidney and/or circulatory failure from an excess of fluid constricting the heart. As non-limiting examples, the systems and methods disclosed herein could also be used to detect clinical conditions such as arrhythmia, cardiac tamponade, SVC syndrome, valvular heart disease (tricuspid regurgitation), kidney failure, obstructive sleep apnea, etc. Moreover, by analyzing other aspects of the video data (e.g. carotid artery pulsations, facial flushing from capillary refill, a patient's breathing) instead of just the JVP, the systems and methods disclosed herein allow for determination of other conditions including respiratory conditions like COPD (chronic obstructive lung disease) exacerbation, asthma exacerbation, sleep apnea, arrhythmias like atrial fibrillation, supraventricular or ventricular tachycardia, etc.

Implementations are described below, by way of example only, with reference to FIGS. 1-6.

FIG. 1 shows a representation of a system for assessment of heart and respiratory disorders in accordance with some aspects of the present disclosure. In the implementation of the system depicted in FIG. 1, a video analysis tool 116a is run as part of an application 116 on a clinician's computing device 110.

As depicted in FIG. 1, a clinician 102 (or other care practitioner, or the patient) takes a video of a neck region of a patient 104. The video data may in particular capture the right-side of the patient's neck region, taken from the front of the patient or the transverse side of the patient. The video analysis tool 116a is able to discriminate between different angles from which the video data is taken for analysis of the video data. The video data may also in particular be captured while the patient 104 is sitting down, and/or while the patient's neck is inclined at a 45 degree angle, though the disclosure is not limited to such arrangement.

The video may be captured using various types of video recording devices, including but not limited to a mobile phone, a tablet, a computer, a digital camera (including cameras with specific optical filters such as for example an IR filter, 3D cameras, stereo cameras, etc.), webcam, etc. As shown in FIG. 1, the clinician 102 uses a mobile phone 106 to record the video, and uploads the video data to the clinician's computer 110. Of course, the video data could instead be captured using the clinician's computer 110 that is running the application (e.g. through a built-in camera), or the mobile phone 106 could instead be running the application 116 and thus there would be no need to upload the data to a separate computing device. The representation of the system shown in FIG. 1 is thus non-limiting.

The video data captured by the mobile phone 106 is uploaded to the clinician's computer 110, which may for example be local to the clinician's office. The computer 110 as shown in FIG. 1 comprises a processing unit (e.g. CPU) 112, a memory 114, non-volatile storage 118, an input/output interface 120, and a communication interface 122. In the system of FIG. 1, the video analysis tool 116a is stored as a component of application 116 in the memory 114 of the computer 110. The application 116 comprises non-transitory computer-readable instructions that, when executed by the CPU 112, configures the computer 110 to perform certain functionality. For example, upon execution of the application 116 the computer 110 may display a user interface of the application for the clinician 102 to interact with, which may for example present instructions for capturing the video data, an interface to upload the video data, an interface to view assessment data, etc. Further, the application 116 causes the CPU 112 to execute the video analysis tool 116a for analyzing the video data.

The clinician 102 may create a profile for the patient 104 in the application 116 and input basic information such as height, weight, age, underlying medical conditions, answers to other intake questions, etc. Such information is supplemental patient data that may be used by the video analysis tool 116a when assessing the video data of the patient 104. Having received the video data, the video analysis tool 116a analyzes the video data to assess the patient 104 for heart and/or respiratory disorders. Specifically, the video analysis tool 116a comprises an AI algorithm that may be trained using previous video data correlated with clinician observation and/or measured physical parameters of patients. Training data may be used to build classification criteria in a signal classifier database 124, which is accessible by the video analysis tool 116a and may for example be stored on the clinician's computer 110 or it may be stored in a distributed manner such as in the cloud. The video analysis tool 116a implements machine learning in that over time, the classification criteria in the signal classifier database 124 may be updated/modified as the video analysis tool 116a receives more patient data and performs more analysis. Further, the AI algorithm in the video analysis tool may apply neural network or deep learning as a classifier then the algorithm is performing classification by itself and there is no classification criteria.

The video analysis tool 116a extracts pulsatile signals in the neck region from the video data and determines pulsatile signals of interest for assessing heart and respiratory disorders in the patient 104. The determination of pulsatile signals of interest may be made by extracting features of a plurality of pulsatile signals and classifying the extracted features, for example by comparing the extracted features against classification criteria in the signal classifier database 124, or by the AI algorithm itself when applying neural network or deep learning as the classifier. The video analysis performed by the video analysis tool 116a is described in more detail herein with respect to FIGS. 4A-4F.

The video analysis tool 116a generates assessment data based on the pulsatile signals of interest, which may be output to the clinician 102, for example via the user interface displayed on the computer 110. In some implementations the assessment data may assist the clinician 102 with determining the existence or level of any heart and/or respiratory disorders in the patient 104, by presenting information which is difficult and/or time consuming for the clinician 102 to determine. In other implementations the assessment data may itself comprise an assessment result indicative of heart and/or respiratory disorders in the patient. The video analysis tool 116a may determine an assessment result by accessing the signal classifier database 124 or through the AI classification. The assessment result may also be presented with other assessment data that allows the clinician 102 to confirm that the assessment result is correct.

The video analysis tool 116a may also determine recommended actions based on the assessment result. The system may comprise a recommended actions database 126. The recommended actions database 126 is accessible by the application 116 running on the clinician's computer 110 and may exist locally or it may be stored in a distributed manner such as in the cloud. The recommended actions database 126 may comprise various actions such as instructions for the patient (e.g. "seek medical attention", "no action required", etc.) and medication prescriptions/adjustments (e.g. prescription type, prescription administration frequency, etc.) that can be output by the application 116 based on the assessment result by the video analysis tool 116a.

The recommended actions database 126 may initially be populated with recommendations from the clinician 102 corresponding to varying degrees of heart and respiratory disorders, but the video analysis tool 116a is configured to be self-learning and can adjust recommended actions as patient data is continuously analyzed. The video analysis tool 116a may ingest the patient data and prescribed recommended actions and be configured to identify patterns therein. In some instances, if an initial recommended action is to "seek medical attention" and the clinician 102 prescribes a treatment accordingly, the application 116 can ingest the treatment data prescribed by the care provider to define future recommended actions to the same patient or to other patients experiencing similar symptoms (as determined by their video data and other patient data). Certain types of parameters/rules can be set by the care provider whereas as the machine learns from these interventions it will adapt further to the changes made to improve its suggestions and then the provider can change the level of user involvement subsequently. For example, the application 116 may output a recommended action to the clinician 102 based on the assessment result from the video analysis tool 116a, but the clinician 102 may adjust the recommended action, and input the actual recommendation back into the application 116. The video analysis tool 116a may use machine learning to identify trends in patient data and previously recommended actions to update the recommended actions database 126 and to better suggest future recommended actions.

Patient data, including the video data, any supplemental patient data, and/or assessment data, as received/generated at the application 116, may be securely stored in a patient data database 128. The patient data database 128 is accessible by the computer 110 and may exist locally (e.g. at the clinician's office) or it may be stored in a distributed manner such as in the cloud. The patient data may be stored in association with a unique identifier for the patient, and patient data from the application 116 may be stored in the patient data database 128 together with existing medical records for the patient (i.e. medical information from visits to the clinician 102 or otherwise received by the clinician 102 that was not obtained through the application 116). The patient data and unique identifier may also be associated with permission information indicative of care providers that are authorized to access the patient data. The patient data in the patient data database 128 may be encrypted, and a care provider with authorization to access the patient data may for example be provided with a decryption key to view the patient data.

With the system shown in FIG. 1, the video analysis tool 116a analyzes the video data and generates assessment data based on determined pulsatile signals of interest for assessment of heart and respiratory disorders. The assessment data is output to the clinician 102 and allows the clinician 102 to make an objective assessment of the patient 104.

Figure 2:
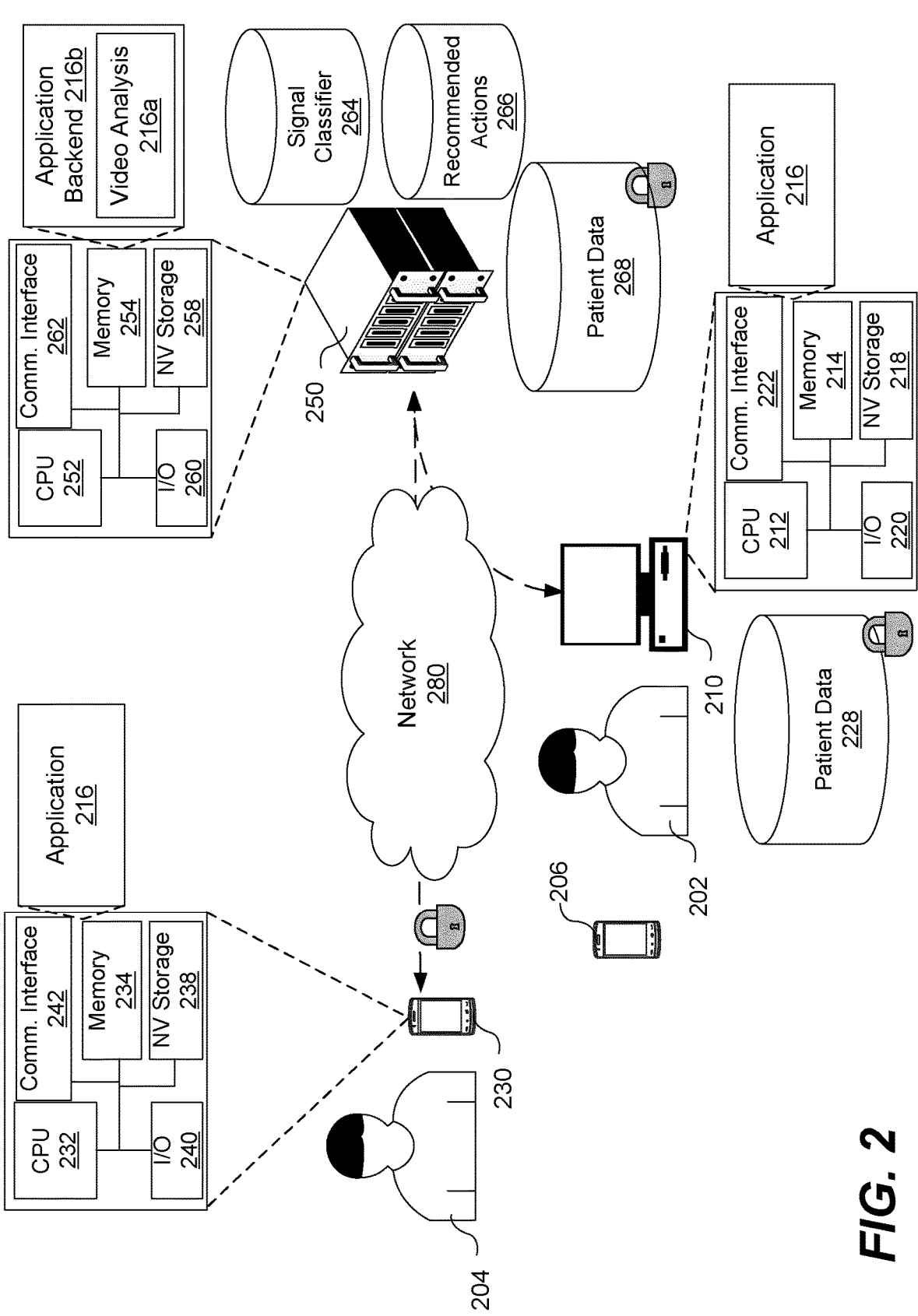
FIG. 2 shows a representation of a system for remote assessment of heart and respiratory disorders in accordance with some aspects of the present disclosure.

FIG. 2 shows a representation of a system for remote assessment of heart and respiratory disorders in accordance with some aspects of the present disclosure. In the implementation of the system shown in FIG. 2, the video analysis tool 216a is executed remotely at a remote analysis system 250.

Similar to FIG. 1, a clinician 202 (or other care practitioner) can take a video of a neck region of a patient 204 using various types of video recording devices, such as mobile phone 206. The video data can be uploaded to the clinician's computing device 210, which is depicted as comprising a processing unit (e.g. CPU) 212, a memory 214, non-volatile storage 218, an input/output interface 220, and a communication interface 222. The memory 214 is depicted as having application 216 stored thereon, which when executed provides a user interface for the clinician 102 to interact with, such as to upload video data, view assessment data, etc. In FIG. 2, the video analysis tool 216a is executed remotely at the remote analysis system 250. The application 216 on the clinician's computing device 210 is supported by the application backend 216b, and the clinician's computing device 210 and the remote analysis system 250 are configured to exchange data over a network 280, such as the Internet. In other implementations, instead of the client's computing device 210 comprising the application 216 stored in memory 214, the clinician's computing device may communicate with the remote analysis system 250 through a web/app portal hosted by the application backend 216b.

Further, the patient 204 can record a video of their neck region using various types of video recording devices, including but not limited to a mobile phone, a tablet, a computer, a digital camera, webcam, etc. As shown in FIG. 2, the patient 204 uses a patient computing device 230 which is a mobile phone to record the video. The patient's computing device 230 (i.e. the mobile phone) comprises several hardware components as shown in FIG. 2, including a processing unit or CPU 232, a memory 234, non-volatile (NV) storage 238, input/output (I/O) devices 240, and a communication interface 242.

The memory 234 stores application 216 as non-transitory computer-executable instructions that can be executed by the CPU 232 to configure the patient's computing device 230 to provide a user interface for the patient 204 to interact with. Additionally or alternatively, as noted above, the patient may access a web/app portal hosted by the application backend 216b in order to exchange data with the remote analysis system 250. The I/O devices 240 of the patient's computing device 230 may include components such as a display for displaying information to the patient 204 or user of the mobile phone, a video recording device such as a camera for recording the video data, a means to receive user input such as a keyboard (if the user cannot interact directly with the display, for example), etc. The I/O devices 240 may also include light sensor technology for measuring a patient's heart rate. Additionally, the I/O devices 240 may include one or more radio beacons that are configured to emit and receive a radio signal (e.g. a low power radio signal) to detect contractility and relaxation of the patient's heart and thereby allow for an accurate determination of the patient's heart rate and electrical pulsations non-invasively and without requiring any sensors hooked-up to the patient. The communication interface 242 of the patient's computing device 230 allows for the exchange of data with other entities over network 280.

The system as implemented in FIG. 2 further comprises the remote analysis system 250, depicted as comprising servers, for facilitating assessment and management of heart and respiratory disorders in the patient 104. The remote analysis system 250 comprises several hardware components as shown in FIG. 2, including a processing unit or CPU 252, a memory 254, non-volatile (NV) storage 258, input/output (I/O) interface 260, and a communication interface 262.

The memory 254 stores application backend 216b as non-transitory computer-executable instructions that can be executed by the CPU 252 to configure the remote analysis system 250 to perform various functionality as described herein. The application backend 216b stored in memory 254 of the remote analysis system 250 comprises the video analysis tool 216a for analyzing video data for the patient 204. As described with reference to FIG. 1, the video analysis tool 216a generates assessment data for providing a determination of heart and/or respiratory disorders in the patient 204, which may include recommended actions for the patient 204. The communication interface 262 of the remote analysis system 250 allows for the exchange of data with other entities over the network 280.

Similar to FIG. 1, the remote analysis system 250 is associated with one or more databases used to store various data/information, such as a signal classifier database 264, a recommended actions database 266, and patient data database 268. In the implementation of FIG. 2, while only one clinician 202 and one patient 204 is shown, a person skilled in the art will readily appreciate that the remote analysis system 250 is configured to facilitate assessment and management of heart and respiratory disorders for a plurality of patients and interact with a plurality of clinicians. Accordingly, as multiple patients and clinicians may interact with the remote analysis system to access data, patient data stored in the patient data database 268 may be securely stored to only allow authorized access. Further, recommended actions in the recommended actions database 266 may be defined for particular clinicians, or may be generalized for all clinicians based on accepted standards.

In the system of FIG. 2, assuming that the patient 204 is a patient of the clinician 202, the clinician 202 may interact with the remote analysis system 250 and access patient data for the patient 204 in the patient data database 268 through the application 216 on the clinician's computing device 210, and/or through a web-portal depending on the implementation of the system. The clinician's computing device 210 used to interact with the remote analysis system 250 is depicted in FIG. 2 as being a computer, however the clinician's computing device is not limited to such and may also be, for example, the mobile phone 206, a tablet, etc. The clinician 202 may enter their credentials (e.g. username and password) into the application 216 or a web portal that is coupled with the application backend 216b, which may be used by the remote analysis system 250 to verify that the clinician 202 has authorization to access requested patient data. The clinician 202 may for example be provided with a summary page for all patients that they are monitoring and for which they have authorization to access their data. The clinician 202 may retrieve patient data from the patient data database 268 and store the patient data in a local patient data database 228 specific to the clinician's office (and which may, for example, encompass existing medical records for patients of the clinician). Some patient data in the patient data database 268 may also be pushed from the remote analysis system 250 to the local patient data database 228.

Figure 6A:
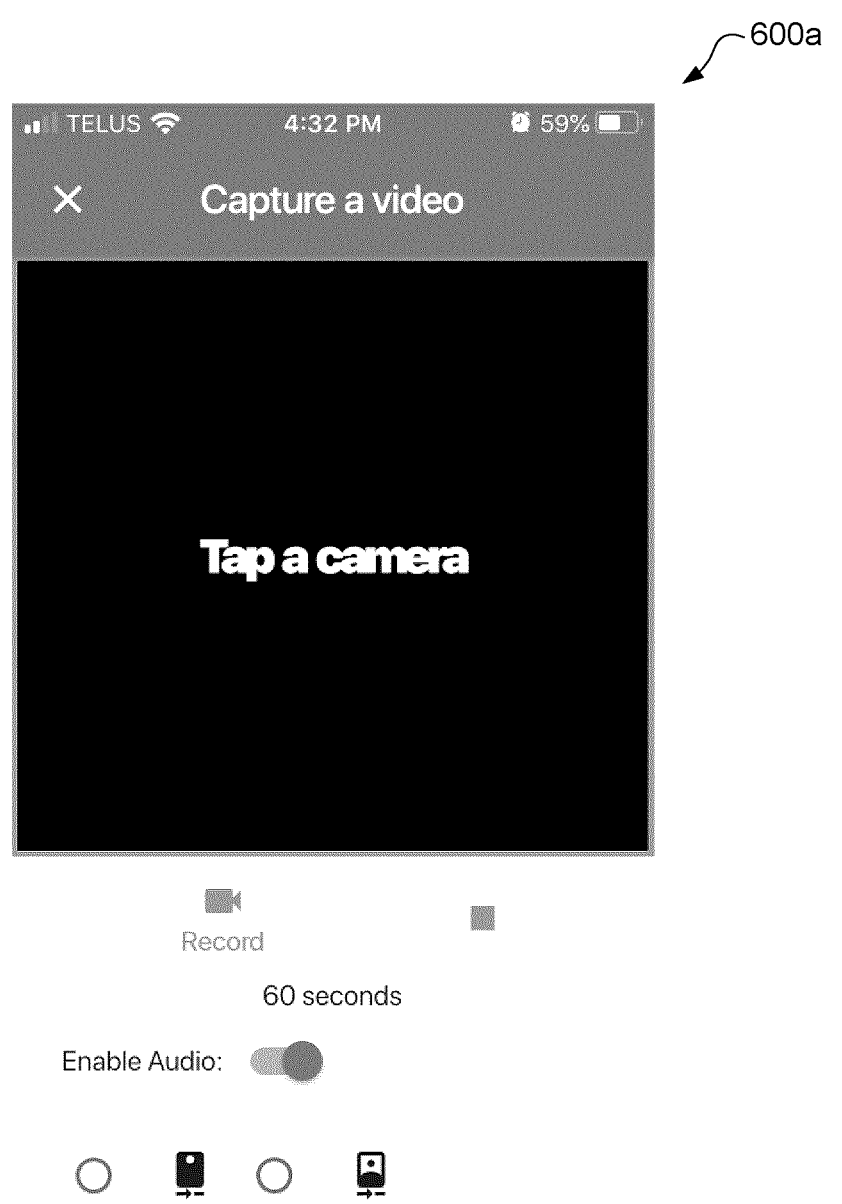
FIGS. 6A-C show screenshots of an exemplary user interface of an application running on the patient's computing device.

In an example use scenario, the patient 204 uses the patient's computing device 230 to record video data of a neck region of the patient 204. For example, video of the neck region may be recorded over a duration that is generally adequate for an assessment of heart and respiratory disorders, e.g. 10-15 seconds or 60 seconds. Generally, the video may be recorded daily, at a consistent time of day, however other frequencies and durations of video recordings are possible. The application 216 running on the patient's computing device 230 may cause a display of instructions for the patient 204 to properly position the patient's computing device 230 to adequately capture the required video for assessment of heart and respiratory disorders. FIG. 6A shows an example of a user interface that may be provided by the application 216 and displayed to the patient 204 for recording video data. This video data is then transmitted over the network 280 to the remote analysis system 250 for analysis. Given the sensitivity of patient health data, the application 216 may cause encryption of the video data prior to transmission and the remote analysis system 250 is configured to decrypt the data upon receipt.

Figure 6B:
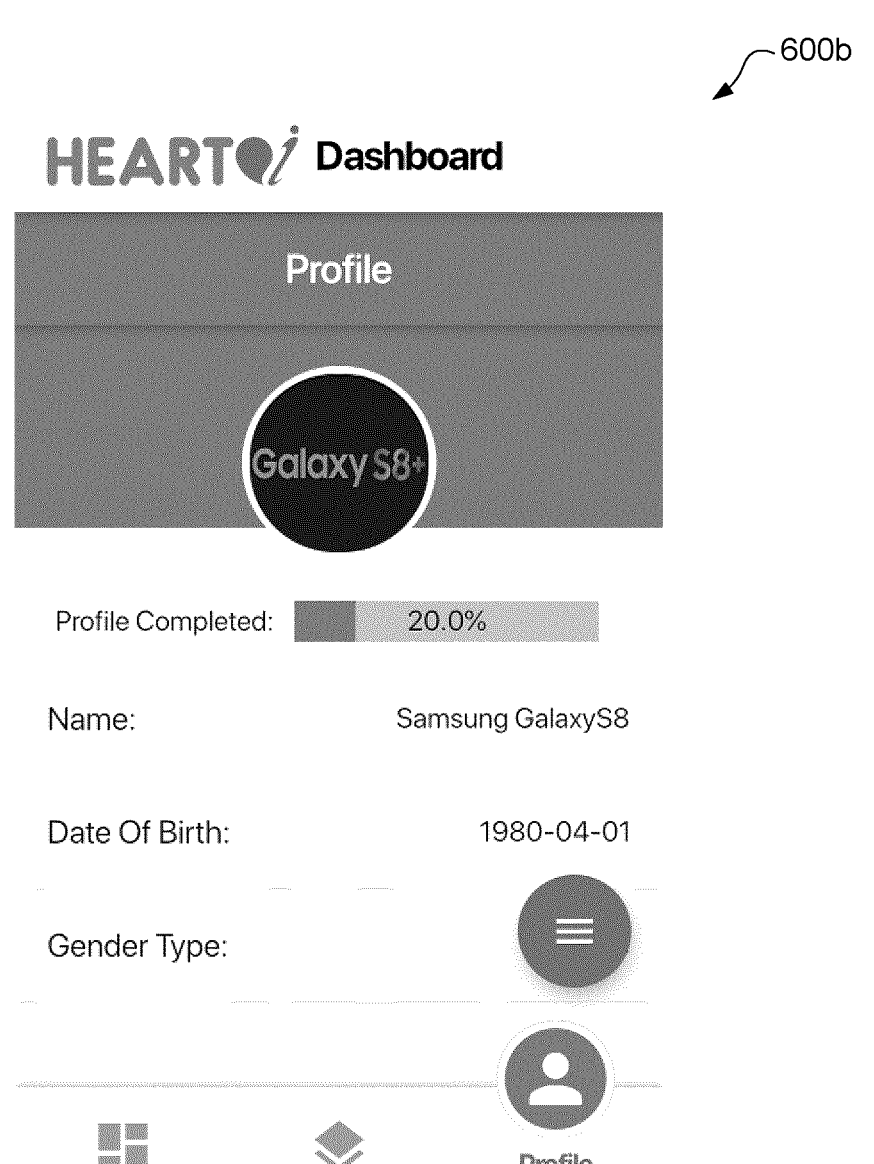
Figure 6C:
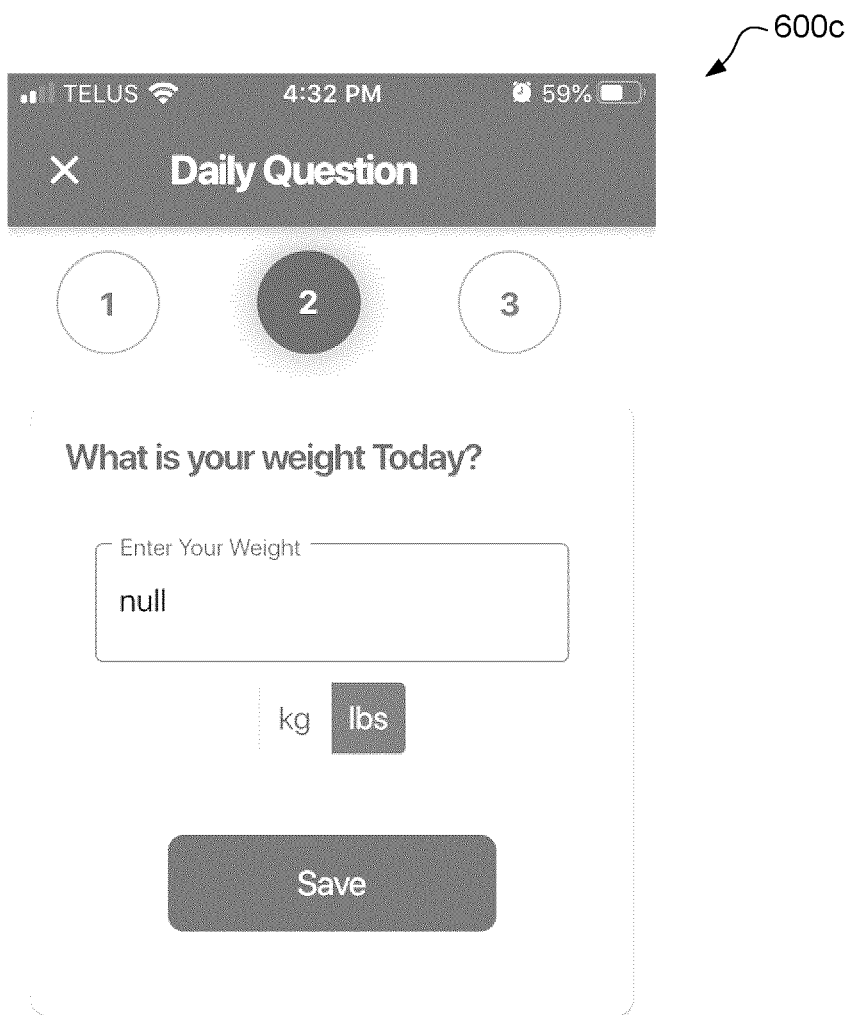

When the application 216 is first downloaded to the patient's computing device 230 the patient 204 may be asked intake questions and required to input basic personal information (e.g. name, age, sex, weight, etc.). Additionally, the patient 204 may be required to answer various questions in order to provide as much information about their cardiac/respiratory conditions as possible. Some questions may for example be presented to the patient 204 daily, and may include, but are not limited to, questions regarding symptoms, heart rate, blood pressure, current treatment, daily weight, etc. Answers to these questions may be manually entered, determined with the electronic device through the application (e.g. the application may initiate using light sensor technology of the device to estimate heart rate), and/or received from an external source (e.g. received from an external measurement device over Wi-Fi™ or other communication network). For example, the patient 204 may be asked whether they have chest pain, shortness of breath, etc., whether they have a current exercise regimen, and whether they are currently taking any medication for their condition. The patient 204 may also be asked these questions throughout their use of the application (e.g. daily, weekly, monthly, etc.). FIG. 6B shows an example of a user interface that may be provided by the application with regards to intake questions. FIG. 6C shows an example of a user interface that may be provided by the application with regards to daily questions. This supplemental patient data may also be transmitted over the network 280 to the remote analysis system 250 for use in the analysis and assessment of heart and respiratory disorders.

Furthermore, as described above, in a non-limiting implementation the patient's computing device 230 may comprise at least one radio beacon for use in accurately estimating the patient's heart rate and cardiac performance. When the patient initiates video capture through the application 216, the patient's computing device 230 may be configured to activate the radio beacon(s) (if they are not continuously emitting/receiving a radio signal) to determine the patient's heart rate and cardiac performance by measuring the contraction and relaxation of the patient's heart. This measured heart rate data and cardiac performance can also be transmitted over the network 280 to the server remote analysis system 250 for use in the analysis and assessment of heart and respiratory disorders. Additionally or alternatively, heart rate measurements may be obtained based on carotid pulsations or even the jugular venous pulsations in the video data (described further herein), and/or using light sensor technology in patient's computing device 230. The heart rate data and cardiac performance, whether being measured continuously or intermittently several times throughout the day, can be merged with the assessment of the video data for the patient 204 to assist with determining levels of heart and/or respiratory disorders. The heart rate and cardiac performance data may be particularly useful in cases where it is technically difficult to make an assessment of a patient (as can occur in short, stocky neck evaluations), and may also be useful in analyzing when patients may be deteriorating in days leading to a congestive heart failure admission.

The remote analysis system 250 is configured to analyze the patient data received from the patient's computing device 230 to generate assessment data for use in assessing heart and respiratory disorders. For example, the video data may be analyzed to identify jugular venous pulsations using the classification criteria in the signal classifier database 264 and/or the AI classification, and assessment data such as a graph showing the pulsations and/or a heat map can be output. The clinician 202, and/or the video analysis tool 216a, may identify that there is abnormally high jugular venous pulsations in the patient 204 and determine a level of congestive heart failure. In some instances, the remote analysis system 250 may make the assessment result, which can be verified by the clinician 202 of the patient 204. Based on the determined level of heart and/or respiratory disorder in the patient 204, the remote analysis system 250 may access the recommended actions database 266 to determine an appropriate recommended action for the patient 204.

In an implementation where all analysis is performed by the remote analysis system 250, the remote analysis system 250 may transmit the assessment data and/or the recommended action to the patient's computing device 230 for display to the patient 204. In this manner, the patient can be provided with an assessment in real-time. In some instances, depending on the determined level of heart or respiratory disorder in the patient 204 or the recommended action for the patient 204, for example, the remote analysis system 250 may send a notification to the patient's clinician 202. The remote analysis system 250 may also update the clinician 202 with other information such as a medication list for subsequent visits with the patient 204. In some implementations, the remote analysis system 250 may be able to automatically schedule an appointment for the patient 204 with the clinician, such as when a recommended action is to visit the clinician 202. In further implementations, the remote analysis system 250 may be configured to communicate with the patient's pharmacist (not shown).

In another implementation where the clinician 202 is involved with the analysis, the remote analysis system 250 may transmit the assessment data to the clinician's computing device 210 for review by the clinician 202, and the clinician 202 may input an assessment result and a recommended action(s) into the application 216. The remote analysis system 250 may then transmit the assessment data and/or the recommended action to the patient's computing device 230 for display to the patient 204. In this manner, the application 216 may act as a communication channel between the patient 204 and the clinician 202, and the patient 204 can receive an assessment without having to physically visit the clinician 202. In a further implementation, instead of immediately transmitting information to the patient 204 or the clinician 202, the remote analysis system 250 may instead provide a notification that information is available to be retrieved as authorized.

The remote analysis system 250 may store the patient data (e.g. video data and supplemental data), assessment data, and any recommended actions in the patient data database 268, and may encrypt the data. The patient data received from the patient's computing device 230 may also include information indicative of the patient, whether a name of the patient 204, a username for the application 216, an identifier of the patient's computing device 230, etc., and accordingly the patient data can be stored in the patient data database 268 in association with a unique identifier for the patient 204.

The remote analysis system 250 may subsequently receive a request from the patient 204 to access the patient data in the patient data database 268 and retrieve the correct patient data. Additionally, the remote analysis system 250 may receive a request from the clinician 202 to access the patient data and/or communicate with the patient. The remote analysis system 250 may be configured to determine whether the clinician 202 has authorization to access the data for the patient 204 based on permission information associated with the patient identifier. The permission information associated with the patient identifier may be provided by the patient using the application. In this manner, the remote analysis system 250 can provide a secure communication channel between the patient 204 and the clinician 202. The patient 204 and the clinician 202 may also be able to communicate with one another, for example through the application 216 or through an online portal provided by the application backend 216b.

In some implementations, whole and/or partial/preliminary analysis of the patient data may be performed at the patient's computing device 230 (and/or the clinician's computing device 210 when the clinician records the video data). The application 216 may comprise computer-executable instructions for performing such data analysis. In some instances, signal classification criteria and/or a list of recommended actions for use with the video analysis may be pushed to the patient's computing device 230 and/or the clinician's computing device 210. The patient data may still be sent to the remote analysis system 250 for storage in the patient data database 268, thus it can be discarded from the patient computing device 230 to conserve memory space. The patient computing device 230 may for example implement a store-and-forward mechanism to transmit the patient data to the remote analysis system 250 when available space in memory becomes low. In this manner, the remote analysis system 250 is still able to perform AI learning using the patient data.

Figure 3:
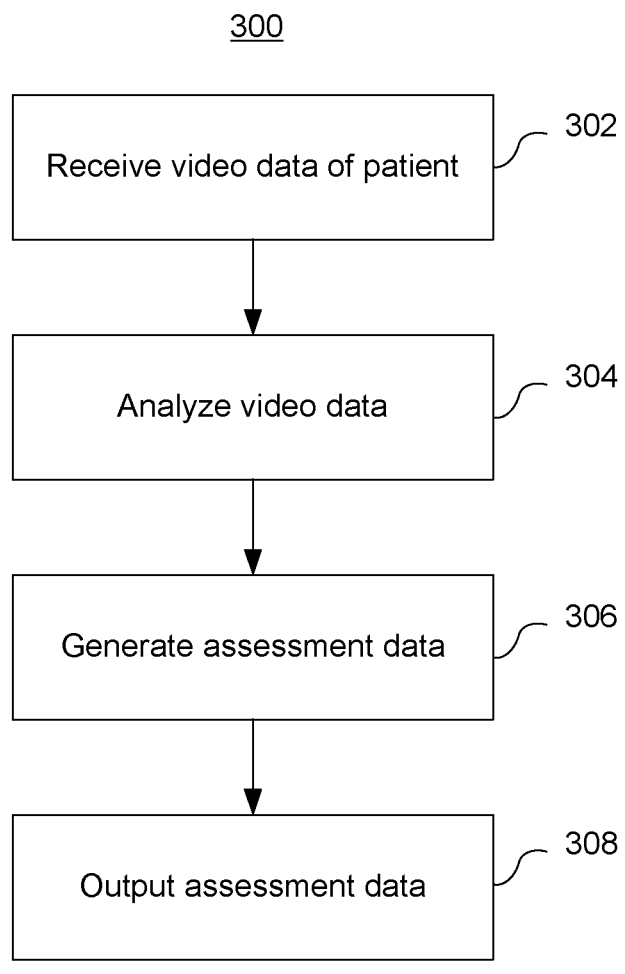
FIG. 3 shows a method performed by a computing device for assessment of heart and respiratory disorders.

FIG. 3 shows a method performed by a computing device for assessment of heart and respiratory disorders. The method 300 may be performed by running the video analysis tool 116a at the clinician's computing device 110 such as shown in the system of FIG. 1, or may be performed by the video analysis tool 216a at the application backend 216b of the remote analysis system 250 such as shown in the system of FIG. 2.

The method 300 comprises receiving video data of a neck region of the patient (302). The video data is of a region of the neck where pulsations can be observed, and may in particular be of the right side of the patient's neck. The received data may also include information indicative of the patient, and supplemental patient data such as answers to questions regarding symptoms, compliance, treatment, etc., as well as heart rate and cardiac performance data as measured from radio technology at the electronic device, for example. The recorded video data, and any other available patient data, is analyzed to determine pulsatile signals of interest in the patient's neck region for assessing heart and respiratory disorders (304) such as pulsations of veins or arteries in the neck as well as pulsations related to the muscle contraction of the sternocleidomastoid and respiratory muscles. Assessment data is generated based on the pulsatile signals of interest (306), which facilitates the assessment of heart and respiratory disorders. The assessment data is output (308), such as being displayed on the clinician's computing device 110 in the system configured as shown in FIG. 1, and/or being transmitted from the remote analysis system 250 to the clinician's computing device 210 and/or the patient's computing device 230 in the system configured as shown in FIG. 2.

In some implementations, the output of the assessment data may comprise graph(s) showing the pulsatile signals of interest, and/or a heat map showing various features related to the pulsations that can be presented to the clinician to assist with assessing the patient. Other information determined from the video analysis, such as an estimate of a height of a column corresponding to jugular venous pulsations, may be output. Additional patient data, such as heart rate or breathing rate and use of accessory muscles, may also be presented. Further, the assessment data may comprise an assessment result and/or recommended actions made by the video analysis tool. The clinician may be able to interact with the assessment data through the UI on their computing device.

Figure 4A:
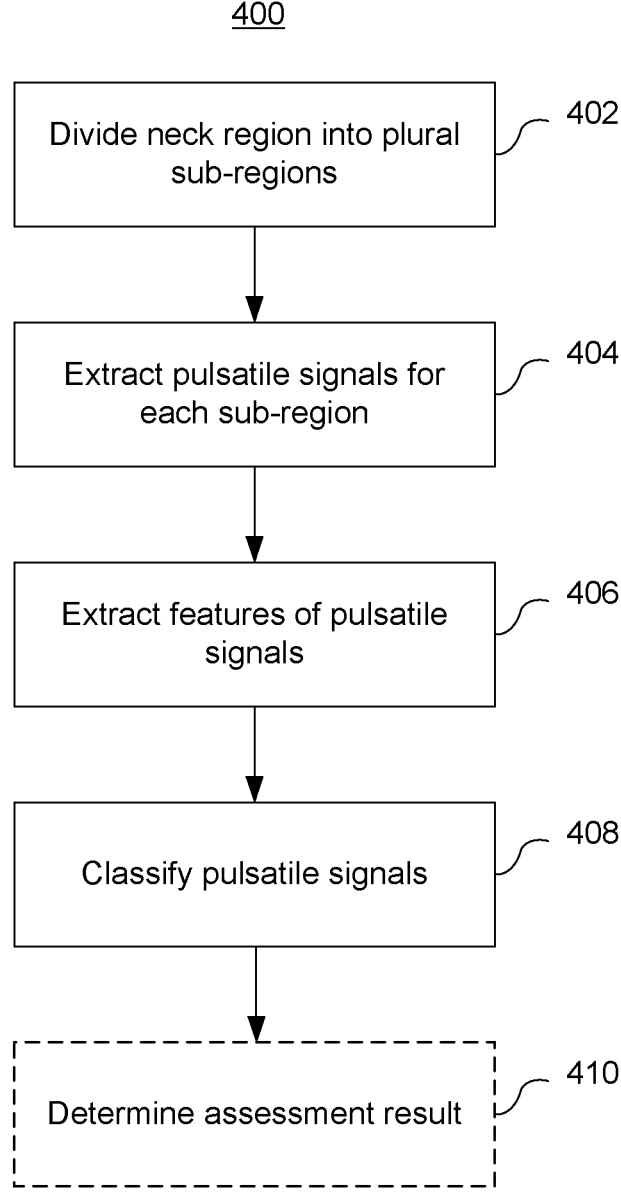
FIGS. 4A-F show methods of analyzing video data to assess heart and respiratory disorders.

FIGS. 4A-F show methods of analyzing video data to assess heart and respiratory disorders. FIG. 4A shows a method of analyzing video data to assess heart and respiratory disorders. The method 400 may be performed by the video analysis tool when analyzing the video data and generating assessment data in 304 and 306 of method 300.

In the method 400, having received the video data of a neck region of the patient, each frame of video data showing the neck region is divided into a plurality of sub-regions (402). Each sub-region may be the same size, and may as a non-limiting example correspond to a block of pixels that is equivalent to a 1 mm×1 mm region of the neck. Each frame of the video data is divided in the same manner so that a sub-region in one frame corresponds to the same sub-region in every other frame of the video data.

A pulsatile signal is extracted for each sub-region (404). Specifically, because the video data is captured over a period of time, such as 10-15 seconds, variations in the pixels contained within each of the sub-regions can be tracked for each frame over the duration of the video data. As the video data is captured over a time period of 10-15 or more seconds, the video data should be sufficient to be taken over several cardiac and respiratory cycles. Variations in the pixels that are tracked for each sub-region may include the movement of pixels and/or the colour of the pixels. The time-series data for each sub-region generally corresponds to a pulsatile signal, though the pulsatile signal of each sub-region will likely vary. Different methods used to track variations in the pixels may be based on the angle of the patient's neck from which the video was recorded. For example, tracking variations of pixel colour may be used when the video is recorded from the front of the patient, and tracking pixel motion may be used when the video is recorded from the side of the patient.

Figure 4B:
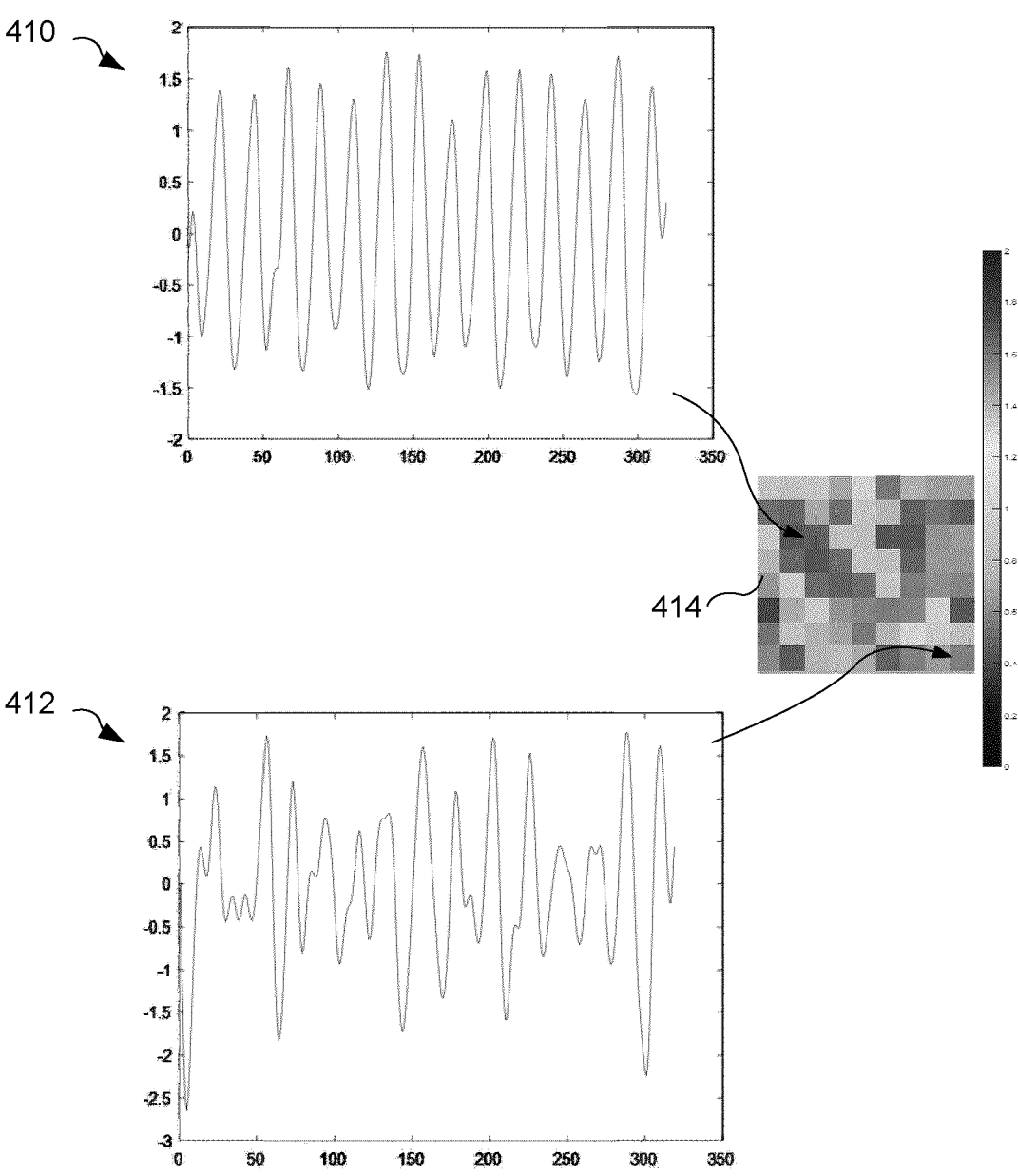

FIG. 4B shows examples of pulsatile signals 410, 412 that have been extracted from two different sub-regions in a frame of video data recorded of the neck region of a patient by tracking variations in pixel colours within each sub-region. An average colour of pixels in the sub-regions can be tracked across the different frames of video data (in this example, there are 319 frames) to obtain the time-series data showing the pulsatile signals 410, 412.

Referring back to the method 400, features of the pulsatile signals are extracted (406). Such features may include statistical features, time domain features, and frequency domain features. Statistical features may include correlation coefficients between different signals that can include correlation coefficients between pulsatile signals themselves from different sub-regions on the neck, pulsatile signal from different sub-regions on the neck with the extracted breathing signal and so on, mean and variance of the extracted modulated respiratory component that is superimposed on the pulsatile signal in each sub-region and so on. Time domain features may include shape of the pulse, time of the rising edge, time difference between pulses, amplitude of the pulse, etc. Frequency domain features may include an amplitude, a frequency, a power level, and a second harmonic, ratio of the amplitude of the first and second harmonics, signal to noise ratio of the pulsatile component of the signal vs. other components in the frequency range of interest, etc. These features are not limited only to Fourier Transform but can be extracted from a number of other transforms.

Each of the pulsatile signals are classified according to their respective features to determine pulsatile signals of interest for assessing heart and respiratory disorders (408). In an implementation, machine learning classifiers may be trained to define classification criteria used in identifying pulsatile signals of interest, and the classifiers may be updated over time as more patient data is received. In another implementation, the video analysis tool may apply a neural network or deep learning as a classifier. Among other things, the classification of pulsatile signals may include identifying whether a pulsatile signal corresponds to a jugular venous pulsation or a carotid artery pulsation.

In the example signals shown in FIG. 4B, the pulsatile signal 410 is indicative of carotid artery pulsations, while the pulsatile signal 412 is indicative of jugular venous pulsations. Various features of the pulsatile signals may be extracted to classify the signals. For example, FIG. 4B depicts a heat map 414 that is generated by analyzing a signal-to-noise ratio based on the signal power of the pulsatile signals for each of the sub-regions. Generation of other heat maps that highlight pulsatile signals of interest are also possible, such as heat maps based on the ratio of power of the second harmonic and the main pulsatile component, heat maps based on the power of the second harmonic, etc. Based on the features of the pulsatile signals (such as the features which are displayed in the heat map), sub-regions and corresponding pulsatile signals can be classified as pulsatile signals of interest for assessment of heart and respiratory disorders.

In a further aspect, the features of the pulsatile signals may also be used to determine additional information such as a heart rate and respiration rate of the patient. In the pulsatile signal 410, there are about 14 pulses in 319 frames with sampling rate of 30 frames per seconds resulting in 14 pulses*60 sec/(319/30)=78 beats per minute. The respiratory rate may be obtained from each sub-region separately or from the overall neck region that includes all the sub-regions. A signal processing algorithm may provide one sample per frame using either tracking changes in color, tracking motion of the pixels or some other algorithm. This signal can then be filtered using a bandpass filter with cut-off frequency corresponds to the minimum and maximum breathing rate. The heart rate and respiration rate may be used to help classify the pulsatile signal.

Figure 4C:
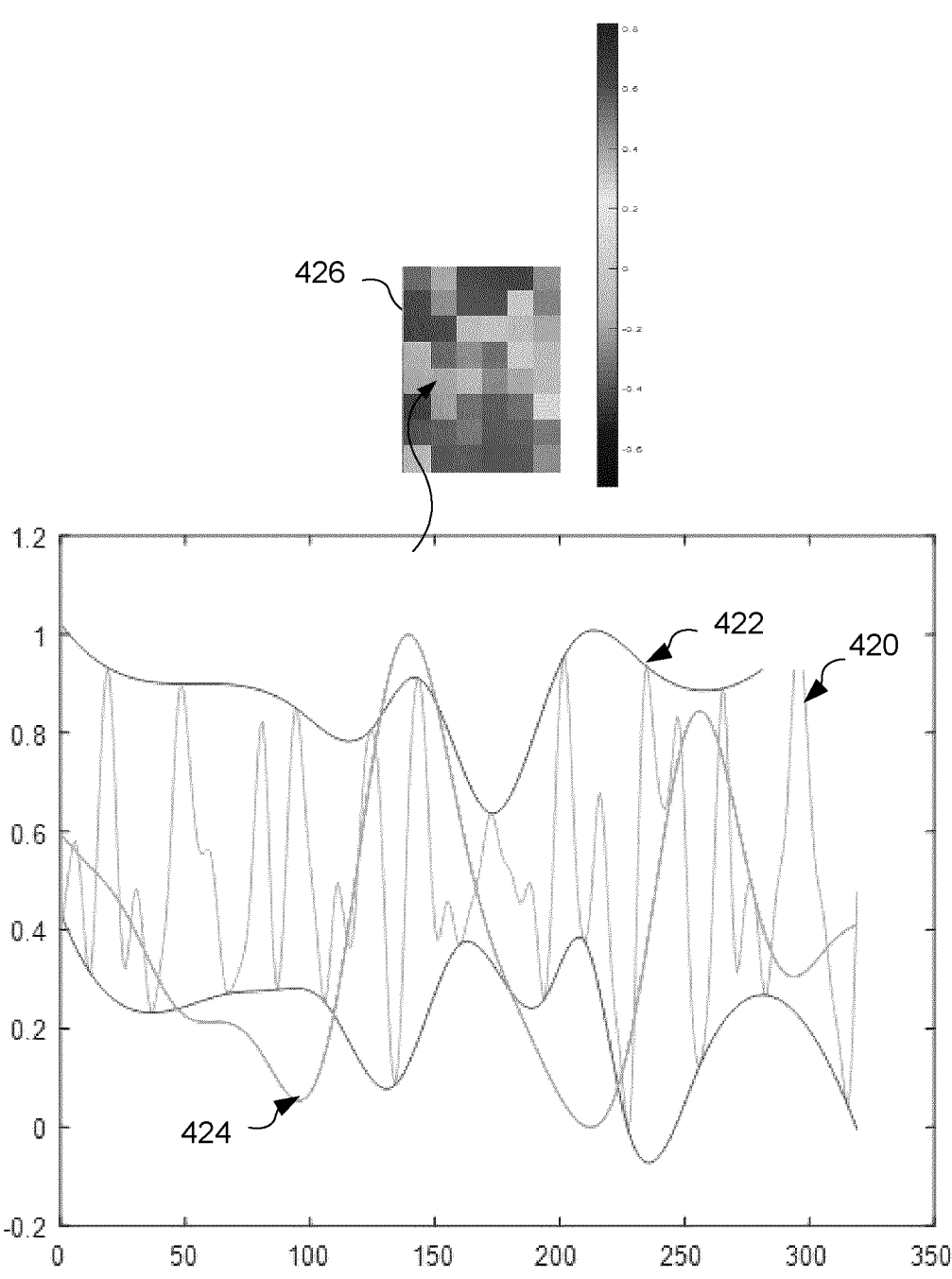

FIG. 4C shows an example of a pulsatile signal 420 that has been extracted from a sub-region in a frame of video data recorded of the neck region of a patient by tracking variations in pixel motion within each sub-region. The envelope of the cardiac signal is represented by line 422, and a respiration signal extracted from the pulsatile signals for all of the sub-regions is represented by line 424. In this example, a correlation coefficient may be computed between the envelope 422 of the pulsatile signal 420 and the extracted respiration signal 424 to assist in classifying whether this particular sub-region is affected by breathing or not, which is shown for each of the plurality of sub-regions in the heat map 426. Other features may also be evaluated to classify the pulsatile signal, such as by evaluating a signal-to-noise ratio for each of the pulsatile signals based on tracking movement of each pixel, extracting the envelope of the cardiac signal, etc.

In the method 300, the generation and output of assessment data in the may comprise one or more of the pulsatile signals of interest (such as signals 410, 412, or 420), an envelope of a cardiac signal such as signal 422, and/or a respiration signal such as signal 424, which may be output to the clinician to facilitate the assessment of heart and respiratory disorders. Additionally or alternatively, the heat maps 414, 426 or other types of heat maps may be generated that highlight the pulsatile signals of interest for output. The heat maps may be overlaid on the neck region of the patient, e.g. in a still image or overlaid on top of the video data. A person skilled in the art will appreciate that generation and output of assessment data may take different forms, and may for example be based on selections made by the clinician in the application indicating information that is of interest, and/or based on the analysis of video data itself (e.g. where the data shows a strong correlation or is indicative of a heart or respiratory disorder, generating and outputting assessment data specific to this aspect).

Further, based on the features of the pulsatile signals of interest, the video analysis tool can provide an assessment of various types of heart and respiratory disorders. The method 400 may comprise determining an assessment result based on the pulsatile signals of interest (410). The heart rate and respiration rate, as well as any supplemental patient data, may also be used in the assessment of heart and respiratory disorders.

Figure 4D:
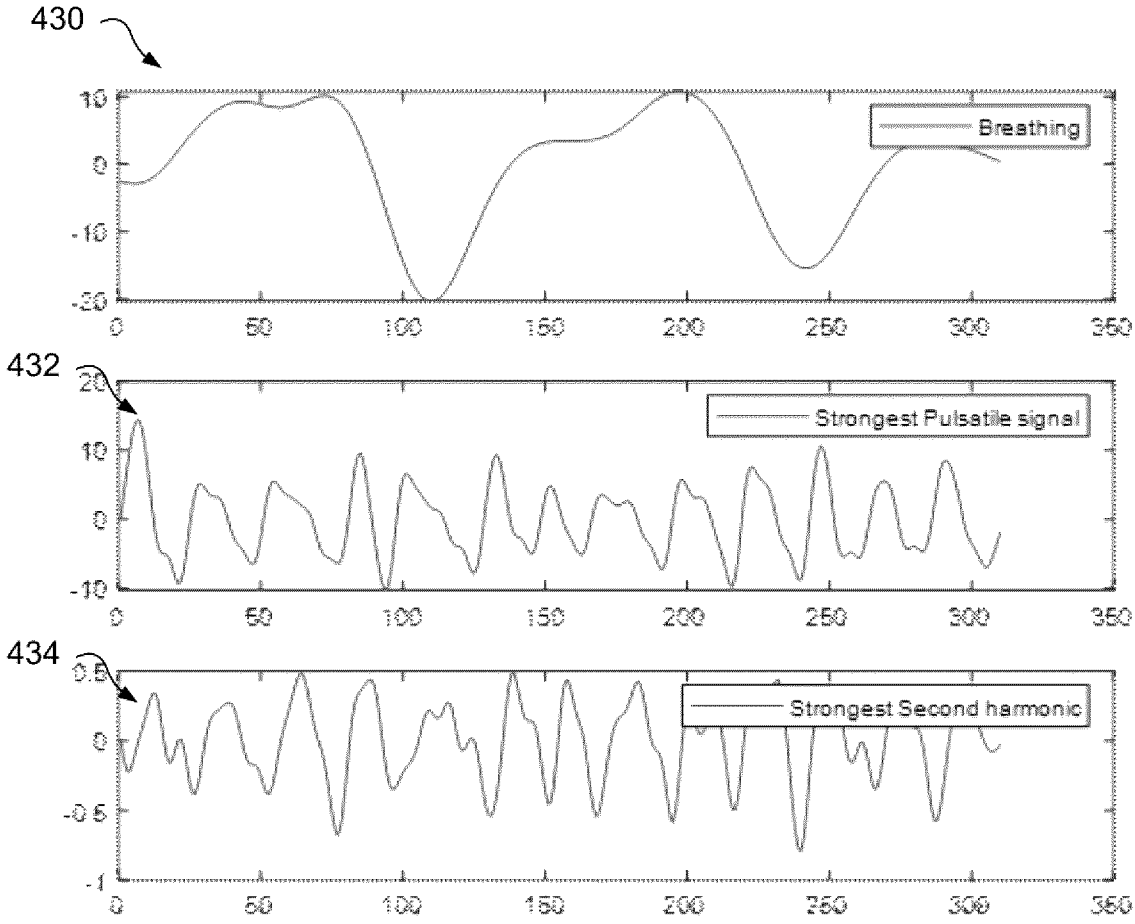

FIG. 4D shows an example of graphs that are indicative of an arrhythmia in a patient. The top graph shows a breathing signal 430 extracted from the plurality of pulsatile signals from the video data. The middle graph shows a strongest pulsatile signal 432 corresponding to carotid artery pulsations. The bottom graph shows a pulsatile signal 434 from a sub-region on the neck that has the strongest second harmonic (assuming that the first harmonic corresponds to the heart rate). The strongest pulsatile signal 432 and the signal with the strongest second harmonic 434 may be generated having previously classified pulsatile signals corresponding to the carotid artery and jugular venous pulsations.

Various types of arrhythmias may be determined based on the nature of the associated peaks and troughs of the jugular relative to the carotid pulse, and more particularly, by an analysis of the variation of the time difference between consecutive pulse peaks. By looking at the time instances of the peaks of the strongest pulsatile signal 432 in the middle graph, the video analysis tool can conclude that the patient is experiencing arrhythmias. Furthermore, the signal with the strongest second harmonic 434 shows a delay in a peak of the venous pulsations compared to the artery pulsations, which may be indicative of tricuspid regurgitation.

Figure 4E:
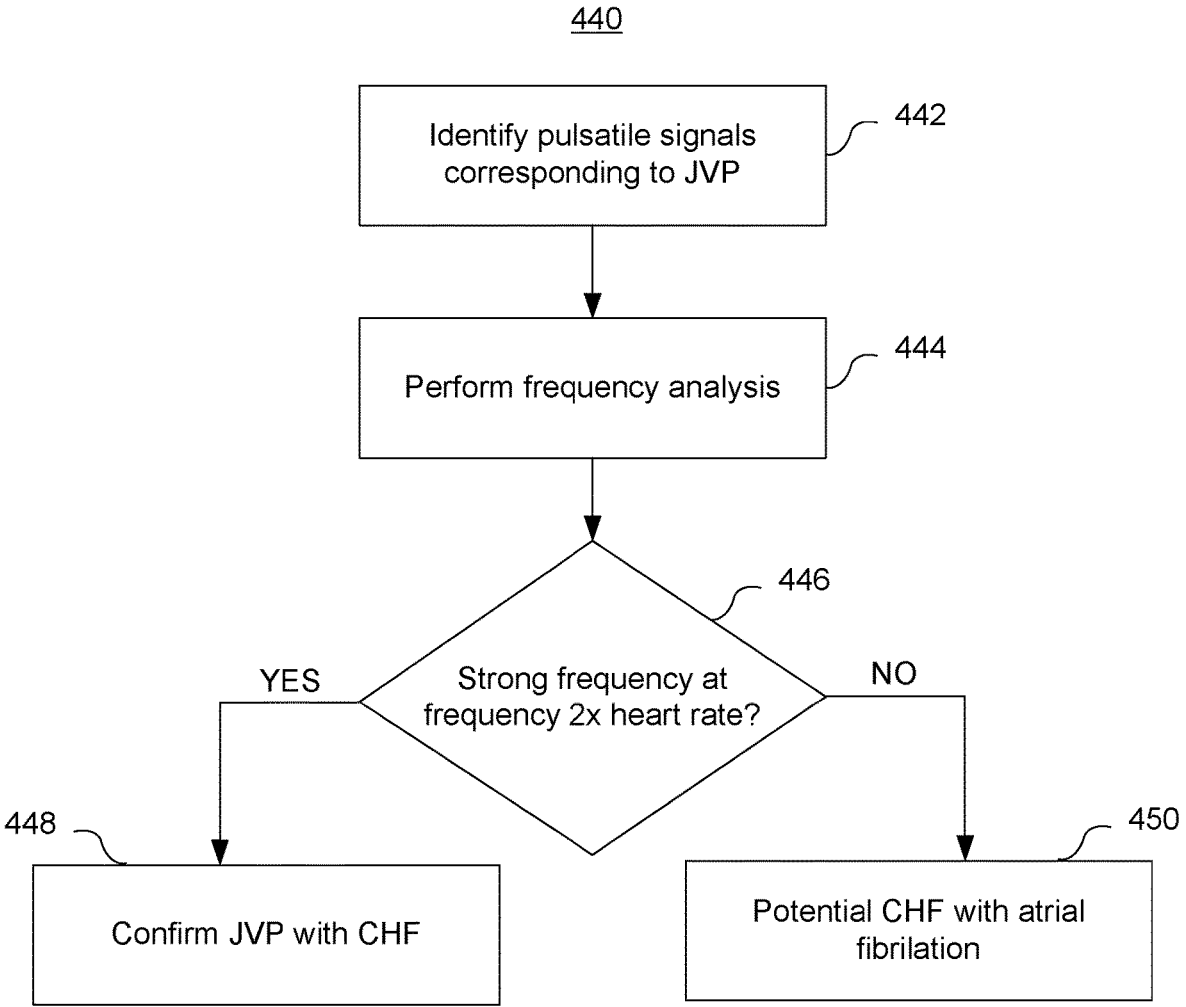

FIG. 4E shows a method 440 as one example that may be used to assess the patient for CHF. In the method 440, pulsatile signals corresponding to jugular venous pulsations are identified (442). The identification of these pulsatile signals may be performed by the classification of pulsatile signals in 408 of the method 400. A frequency analysis is performed on the pulsatile signals corresponding to jugular venous pulsations (444). A determination is made if there is a strong frequency component at a frequency that is about twice larger than the heart rate (446). If there is a strong frequency component (YES at 446), a determination may be made that the patient is experiencing CHF (448). If there is not a strong frequency component (NO at 446), a determination of potential CHF with atrial fibrillation may be made based on the shape of the pulse (450). Jugular pulsations generally have a biphasic appearance in the setting of a normal rhythm (called sinus rhythm). Therefore, when an arrhythmia develops like atrial fibrillation, one loses one of the two peaks on the jugular vein. Therefore, if the jugular vein is clearly distinguished from the carotid artery, coupled with the presence of symptoms (which may be confirmed by the questions answered by the patient in the application), then one can subsequently determine the severity of the heart failure decompensation depending on whether the vein is identified in the sitting position versus a less acute angulation (semi-recumbent position) such as perhaps in a 45 degree seated position or varying degrees of a semi recumbent position.

Figure 4F:
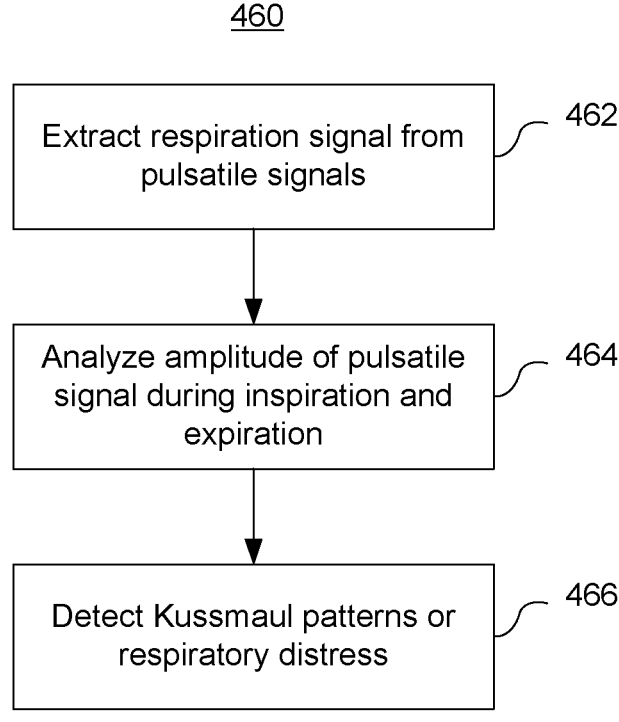

FIG. 4F shows a method 460 as one example of detecting Kussmaul patterns or respiratory distress. In the method 460, a respiration signal is extracted from the pulsatile signals (462). The amplitude of the pulsatile signal for pulsatile signals corresponding to jugular venous pulsations is analyzed during inspiration and expiration (464). Kussmaul patterns or respiratory distress may be detected from the analysis (466), which may in turn be indicative of various types of heart disorders. Often patients with extreme swings in intrathoracic pressures will lead to a significant change in the jugular venous pulsations making them appear and disappear in a sitting position. Other respiratory conditions may also be detected from the extracted respiration signal on its own.

As evident from the foregoing description, a person skilled in the art will appreciate that many different features can be used to classify pulsatile signals as pulsatile signals of interest, and that assessment results indicative of various types of heart and respiratory disorders can be determined based on features of the pulsatile signals of interest as well as other information extracted from the video data (such as heart rate, breathing rate, carotid uptake, etc.) and supplemental patient data (e.g. age, weight, etc.) that is received. Moreover, other information can be extracted from the video data, such as the degree of shortening and lengthening of the sternocleidomastoid excursion (suggestive of respiratory distress with the use of accessory muscles), use of the thyroid cartilage (i.e. the Adam's apple) as a landmark to assess the elevation of the jugular vein relative to the clavicle and earlobe, facial flushing to confirm the carotid pulsation (and jugular with second harmonic) and able to distinguish the region of interest as belonging to the carotid versus the JVP pulsations in the neck. As such, the specific examples of video analysis provided herein are for the sake of explanation and are non-limiting.

The machine learning aspects of the video analysis tool may also consider trends in the patient data to make assessments (e.g. deteriorating conditions in the patient over the course of a week). Thus, the assessment result may be further based on historical assessment data generated from previously received video data. That is, besides features extracted from the current video recording, the historical features extracted from the previous video recordings together with other patient history will we used to come up with the assessment results.

Figure 5:
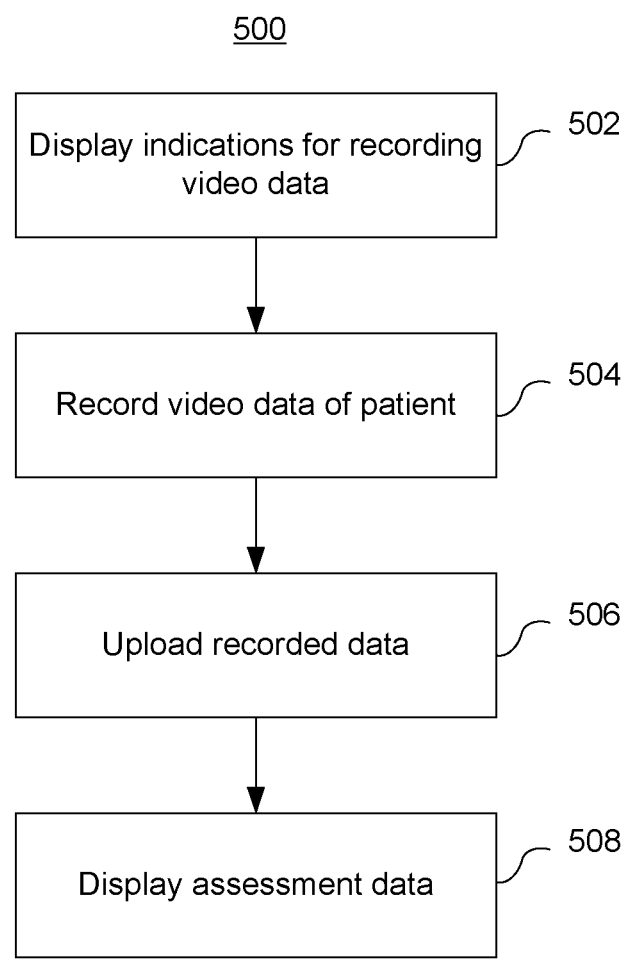
FIG. 5 shows a method performed by a computing device for facilitating assessment of heart and respiratory disorders.

FIG. 5 shows a method performed by a computing device for facilitating assessment of heart and respiratory disorders. The method 500 may be performed by running the application 116, 216 on the clinician's computing device 110, 210 or the patient's computing device 230 when used for capturing video data.

The method 500 comprises displaying indications on a display of the computing device to a user for positioning the electronic device to record video data indicative of pulsations in a neck area of the patient (502). A user of the computing device initiates recording of video data indicative of pulsations (504). The recorded video data is uploaded for analysis (506), for example to the application 116 on the clinician's computer 110 when the video analysis tool is stored thereon, or to the remote analysis system 250 when analysis is performed remotely. The data provided to the video analysis tool also includes information indicative of the patient. As described previously, additional patient data may also be input into the application for analysis by the video analysis tool, including supplemental patient data providing answers to questions regarding symptoms, compliance, treatment, etc., and heart rate data and cardiac performance as measured from radio technology, for example. Assessment data generated by the video analysis tool is displayed (508). The assessment data may comprise one or more graph(s), heat map(s), an assessment result, and/or a recommended action. If the video analysis tool is remote from the computing device, the computing device may receive the assessment data, which may be encrypted.

FIGS. 6A-C show screenshots of an exemplary user interface of an application running on the patient's computing device. FIG. 6A shows a screenshot 600a directing the user to capture a video. This screen may also display to the user various instructions (not shown) as previously described to assist with the video capture. FIG. 6B shows a screenshot 600b for developing a profile of the patient. As previously described, such intake data may be input when an account for the patient is first created. FIG. 6C shows a screenshot 600c of additional questions that may be presented to the user (e.g. daily questions).

It would be appreciated by one of ordinary skill in the art that the system and components shown in the figures may include components not shown in the drawings. For simplicity and clarity of the illustration, elements in the figures are not necessarily to scale, are only schematic and are non-limiting of the elements structures. It will be apparent to persons skilled in the art that a number of variations and modifications can be made without departing from the scope of the invention as described herein.

The invention claimed is:

1. A computer-implemented method for assessing heart and respiratory health in a patient, comprising:
   receiving video data of a neck region of the patient captured by a video recording device;
   generating, with a video analysis tool, assessment data indicative of heart and/or respiratory health in the patient, wherein generating the assessment data comprises:
      segmenting the video data into a plurality of sub-regions, each of the plurality of sub-regions depicting a sub-region of the neck region and corresponding to a region in the video data;
      extracting a plurality of pulsatile signals corresponding to an artery or a vein in the neck region, wherein a pulsatile signal is extracted from each of the plurality of sub-regions of the video data by tracking variations of pixel color and/or pixel movement in each sub-region of the video data to generate a plurality of times-series data corresponding to the plurality of pulsatile signals, each of the plurality of times-series data corresponding to one of the plurality of pulsatile signals;
      extracting features corresponding to pulsatile signal features and comprising statistical features, time domain features, frequency domain features, or combinations thereof from each of the plurality of times-series data;
      classifying one or more pulsatile signals of the plurality of pulsatile signals as pulsatile signals of interest indicative of the heart and/or respiratory health in the patient based on the extracted features and classifying one or more of the pulsatile signals of interest as either a jugular venous pulsation or a carotid artery pulsation; and
      generating the assessment data indicative of heart and/or respiratory health in the patient based on the pulsatile signals of interest and the extracted features; and
   outputting the assessment data indicative of heart and/or respiratory health in the patient,
   wherein the assessment data comprises: a heat map of the neck region of the patient highlighting the pulsatile signals of interest and the jugular venous pulsation.

2. The method of claim 1, further comprising determining an assessment result of heart and/or respiratory disorder in the patient based on the pulsatile signals of interest, wherein the assessment data comprises the assessment result.

3. The method of claim 2, further comprising:
   determining at least one of a heart rate and a respiration rate of the patient from the video data based on the pulsatile signals of interest; and
   wherein determining the assessment result is further based on the at least one of the heart rate and the respiration rate, and wherein the assessment data comprises one or both of the heart rate and the respiration rate.

4. The method of claim 2, further comprising at least one of:
   receiving supplemental patient data for the patient, wherein determining the assessment result is further based on the supplemental patient data; and
   determining the assessment result further based on historical assessment data generated from previously received video data.

5. The method of claim 2, wherein the assessment result is an arrhythmia, determined based on a time difference between consecutive pulse peaks of the pulsatile signals of interest.

6. The method of claim 2, further comprising:
   determining a recommended action based on the assessment result; and
   wherein the assessment data comprises the recommended action.

7. The method of claim 1, wherein the features extracted from the pulsatile signal include one or more of: a signal to noise ratio, an amplitude, a frequency, a shape of a pulse, a power level, and a second harmonic of the pulsatile signal.

8. The method of claim 1, wherein the video data is received from a remote computing device, and wherein outputting the assessment data comprises transmitting the assessment data to the remote computing device for display.

9. A non-transitory computer-readable medium having computer-readable instructions stored thereon, which when executed by a processing device, configure the processing device to perform the method of claim 1.

10. The method of claim 1, wherein the heatmap is generated by analyzing signal to noise ratio based on a signal power of the plurality of pulsatile signals and/or based on a ratio of power based on a power of a second harmonic from each of the plurality of pulsatile signals.

11. The method of claim 1, wherein the features extracted from the pulsatile signal comprises an envelope of a cardiac signal, the method further comprising, for each sub-region: computing a correlation coefficient between the envelope and a respiratory signal to classify a respective sub-region as affected by breathing or not affected by breathing.

12. The method of claim 1, wherein the assessment result comprises a determination of cognitive heart failure, determined based on a frequency of the jugular venous pulsation and heart rate.

13. A system for assessing heart and respiratory health in a patient, comprising:

a processing unit; and a memory having computer-readable instructions stored thereon, which when executed by the processing unit, configure the system to:

receive video data of a neck region of the patient captured by a video recording device;

generate, with a video analysis tool, assessment data indicative of heart and/or respiratory heath in the patient, wherein generating the assessment data comprises:

segmenting the video data into a plurality of sub-regions, each of the plurality of sub-regions depicting a sub-region of the neck region and corresponding to a region in the video data;

extracting a plurality of pulsatile signals corresponding to an artery or a vein in the neck region, wherein a pulsatile signal is extracted from each of the plurality of sub-regions of the video data by tracking variations of pixel color and/or pixel movement in each sub-region of the video data to generate a plurality of times-series data corresponding to the plurality of pulsatile signals, each of the plurality of times-series data corresponding to one of the plurality of pulsatile signals;

extracting features corresponding to pulsatile signal features and comprising statistical features, time domain features, frequency domain features, or combinations thereof from each of the plurality of times-series data;

classifying one or more pulsatile signals of the plurality of pulsatile signals as pulsatile signals of interest indicative of the heart and/or respiratory health in the patient based on the extracted features and classifying one or more of the pulsatile signals of interest as either a jugular venous pulsation or a carotid artery pulsation; and generating the assessment data indicative of heart and/or respiratory health in the patient based on the pulsatile signals of interest and the extracted features; and output the assessment data indicative of heart and/or respiratory health in the patient, wherein the assessment data comprises: a heat map of the neck region of the patient highlighting the pulsatile signals of interest and the jugular venous pulsation.

14. The system of claim 13, wherein the system is further configured to determine an assessment result of heart and/or respiratory disorder in the patient based on the pulsatile signals of interest, and wherein the assessment data comprises the assessment result.

15. The system of claim 14, wherein the system is further configured to:

determine at least one of a heart rate and a respiration rate of the patient from the video data based on the pulsatile signals of interest; and wherein determining the assessment result is further based on the at least one of the heart rate and the respiration rate, and wherein the assessment data comprises one or both of the heart rate and the respiration rate.

16. The system of claim 14, wherein the system is further configured to at least one of:

receive supplemental patient data for the patient, wherein determining the assessment result is further based on the supplemental patient data; and determine the assessment result further based on historical assessment data generated from previously received video data.

17. The system of claim 14, wherein the assessment result is an arrhythmia, determined based on a time difference between consecutive pulse peaks of the pulsatile signals of interest.

18. The system of claim 14, wherein the system is further configured to:

determine a recommended action based on the assessment result; and wherein the assessment data comprises the recommended action.

19. The system of claim 13, wherein the features extracted from the pulsatile signal include one or more of: a signal to noise ratio, an amplitude, a frequency, a shape of a pulse, a power level, and a second harmonic of the pulsatile signal.

20. The system of claim 13, wherein the video data is received from a remote computing device, and wherein outputting the assessment data comprises transmitting the assessment data to the remote computing device for display.

21. The system of claim 13, wherein the heatmap is generated by analyzing signal to noise ratio based on a signal power of the plurality of pulsatile signals and/or based on a ratio of power based on a power of a second harmonic from each of the plurality of pulsatile signals.

22. The system of claim 13, wherein the features extracted from the pulsatile signal comprises an envelope of a cardiac signal, the method further comprising, for each sub-region: computing a correlation coefficient between the envelope and a respiratory signal to classify a respective sub-region as affected by breathing or not affected by breathing.

23. The system of claim 13, wherein the assessment result comprises a determination of cognitive heart failure, determined based on a frequency of the jugular venous pulsation and heart rate.

* * * * *